United States Patent [19]

Yoon

[11] Patent Number: 4,485,814
[45] Date of Patent: Dec. 4, 1984

[54] ONE-PIECE COMPOUND ELASTIC OCCLUDING MEMBER

[76] Inventor: In B. Yoon, 2213 Forest Ridge Rd., Timonium, Md. 21093

[21] Appl. No.: 72,683

[22] Filed: Sep. 5, 1979

[51] Int. Cl.³ ............................................. A61B 17/12
[52] U.S. Cl. ..................................... 128/327; 128/346
[58] Field of Search .................. 128/303 A, 325, 326, 128/327, 346; 251/3, 10; 24/129 D, 255 R, 3 M, 17 B, 18, 73 A, 252 A, 30.5 R, 30.5 P, 30.5 L

[56] References Cited

U.S. PATENT DOCUMENTS

| | | | |
|---|---|---|---|
| 2,619,964 | 12/1952 | Thaete | 128/303 A |
| 2,942,604 | 6/1960 | Gravlee | 128/303 A |
| 2,970,596 | 2/1961 | Hamilton | 128/326 |
| 3,001,254 | 9/1961 | Schumm | 24/30.5 PB |
| 3,279,996 | 10/1966 | Long | 167/82 |
| 3,687,138 | 8/1970 | Jarvik | 128/326 |
| 3,726,278 | 4/1973 | Scott | 128/303 A |
| 3,726,279 | 4/1973 | Barefoot et al. | 128/327 |
| 3,760,810 | 9/1973 | Van Hoorn | 128/326 |
| 3,870,048 | 3/1975 | Yoon | 128/326 |
| 3,911,923 | 10/1975 | Yoon | 128/303 A |
| 4,167,188 | 9/1979 | Lay et al. | 128/326 |

FOREIGN PATENT DOCUMENTS 649226 1/1951 United Kingdom ................ 128/346

Primary Examiner—Michael H. Thaler
Attorney, Agent, or Firm—Robert E. Bushnell

[57] ABSTRACT

A one-piece, compound elastic member comprising two substantially solid, like bodies, each having a central aperture, the apertures being expandable for receiving a tubular anatomical structure drawn therethrough, each body being composed of elastic, non-tissue reactive material for applying symmetrical radial inward pressure on the tubular structure, when released to the force of the elasticity, the bodies having an operative position and a rest position and an integral, elastic interconnection between the two bodies, the interconnection being under stress in the operative position of the bodies for urging the bodies in the operative position back into the rest position and for thereby applying asymmetrical pressure on the tubular structure, whereby an anatomical tubular structure drawn through the apertures while expanded, and in the operative position, is ligated by the release of the apertures to the elasticity of the bodies and the release of the bodies to the elasticity of the interconnection.

24 Claims, 14 Drawing Figures

ONE-PIECE COMPOUND ELASTIC OCCLUDING MEMBER

BACKGROUND OF THE INVENTION

The present invention relates to an elastic occluding member for application to an anatomical tubular structure to cause its ligation. More particularly, the present invention is concerned with occluding members having utility for application by a mechanical device to the Fallopian tubes to effect selectively either the temporary or permanent sterilization of the human female.

Since oral and mechanical birth control devices are not always used faithfully, or fail to work in some instances, various procedures have been proposed for effecting the sterilization of both women and men. However, many of these techniques are unpopular because of the resulting complications, the high expense, and because of the general unacceptability among the populace of effecting a sterilization which is permanent, i.e., cannot be reversed. Nevertheless, sterilization is obviously an effective means for solving various problems of population explosion and of voluntarily limiting the size of the family where desired on the part of the parents. Accordingly, research into finding various techniques and instruments for this purpose has continued both under private and government support.

It is now known to apply a single elastic ring occluding member to a Fallopian tube by drawing a portion of the tube into the barrel of an applicator, having the ring member loaded on the outside of the barrel under tension, to form a knuckle in the tube and then forcing the elastic ring member off the barrel and around the knuckle to ligate the tube and effect sterilization of the female.

Such sterilization may be temporary if the elastic forces on the knuckle permit blood to flow through the occluding portion of the knuckle. In this case the elastic ring may be removed later and normal function will return.

Apparatus and methods for applying such an elastic member are disclosed in U.S. Pat. Nos. 3,870,048 and 3,911,923 granted to the inventor of the present invention.

Elastic occluding members presently available, while usually satisfactory, have caused some problems due to the infinitely varying sizes of the anatomical tubular structures sought to be ligated. As a practical matter, the ring-like occluding member may be manufactured in only a limited number of sizes. It may happen that the applied occluding member is too loose and fails in its purpose, for example, by allowing the tiny egg to advance through the knuckle of the Fallopian tube. It is also even possible for a very small Fallopian tube to work its way out of the occluding member in the normal activity of the body members.

SUMMARY OF THE INVENTION

It is therefore a principal object of the invention to improve elastic occluding devices.

It is a more specific object of the invention to provide elastic occluding members which are effective regardless of variations in the size of the ligated anatomical tubular structure.

It is also an object of the invention to provide elastic occluding members which may be applied directly around the neck of the fimbria without forming a knuckle in the Fallopian tube.

These and other objects have been accomplished by a one-piece, compound elastic occluding member comprising first means for applying symmetrical radial inward pressure on the anatomical tubular structure and second means for simultaneously applying asymmetrical pressure on the tubular structure.

More specifically, the one-piece compound, elastic member of the invention comprises two substantially solid, like bodies, each having a central aperture, the apertures being expandable for receiving an anatomical structure drawn therethrough, each body composed of elastic, non-tissue reactive material for applying symmetrical radial inward pressure on the tubular structure, when released to the force of elasticity of the body, the bodies having an operative position and a rest position; and an integral, elastic interconnection between the two bodies, the interconnection being under stress in the operative position of the bodies for urging the bodies in the operative position back into the rest position and for thereby applying asymmetrical pressure on the tubular structure, whereby an anatomical tubular structure drawn through the apertures while expanded, and in the operative position, is ligated by the release of the apertures to the elasticity of the bodies and the release of the bodies to the elasticity of the interconnection.

The accompanying drawings, which are incorporated in and constitute a part of the invention and, together with the description, serve to explain the principles of the invention.

DESCRIPTION OF THE PREFERRED EMBODIMENTS

Reference will now be made in detail to the present preferred embodiment of the invention, an example of which is illustrated in the accompanying drawings.

The one-piece, compound elastic occluding member of the invention for ligating an anatomical tubular structure comprises first means for applying symmetrical, radial, inward pressure on the tubular structure and second means for simultaneously applying asymmetrical lateral pressure on the tubular structure.

Figure 1A:
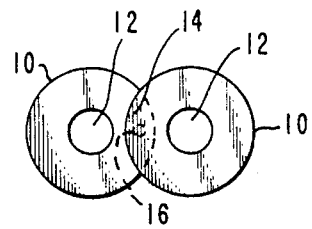
FIGS. 1A and 1B show, respectively, a top view and a cross-sectional view of one embodiment of the one-piece, compound elastic occluding member of the invention.
Figure 1B:
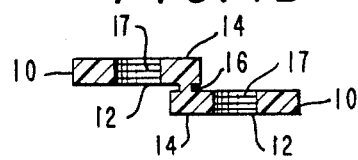

The means for applying symmetrical radial inward pressure on the tubular structure includes two substantially solid, like bodies, each having a central aperture, the apertures being expandable for receiving the tubular structure drawn therethrough; each of the bodies being composed of elastic, non-tissue reactive material for non-reactive continued contact with tissue of the anatomy, the bodies having an operative position and a rest position. In the preferred embodiment as shown in FIGS. 1A and 1B, the substantially solid,like bodies 10, each has a central aperture 12. The elastic, non-tissue reactive bodies are preferably annular in shape and formed of a synthetic material such as teflon or silicone rubber. The annular discs 10 lie in parallel planes and in the rest position of the discs have overlapping segment portions 14. In the operative position of the discs, the discs are substantially congruent and the apertures 12 are aligned.

The means for simultaneously applying asymmetrical, lateral pressure on the tubular structure includes an integral, elastic, interconnection between the like bodies, the interconnection being under stress in the operative positions of the bodies for urging the bodies in the operative positions back to the rest positions and thereby for applying asymmetrical pressure on the tubular structure drawn through the apertures of the bodies.

Figure 2A:
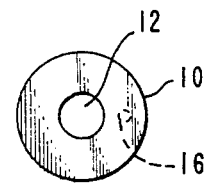
FIGS. 2A and 2B show views like FIGS. 1A and B of a second embodiment of the invention.
Figure 2B:
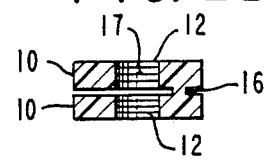

In the preferred embodiment, the segment portions 14 of the discs are integrally joined by an elastic interconnection 16. When the annular discs 10 are in the rest position, the interconnection 16 is not under stress, but when the discs are rotated 180°, with respect to each other, to the operative position, the elastic interconnection 16 is put under stress tending to return the discs to the rest position. It might be noted that FIGS. 2A and 2B, showing the second embodiment of the invention, also depict the embodiment of FIGS. 1A and 1B in the operative position. When the discs 10 are in the operative position and expanded by an applicator known in the art, such as taught in U.S. Pat. No. 3,870,048 or 3,911,923, an anatomical tubular structure can be drawn therethrough.

When the one-piece, compound occluding member is forced off the applicator, the released elasticity of the annular discs tends to ligate the tubular structure drawn through the aperture 12. At the same time, the tendency of the discs to return to the rest position under the resiliency of the interconnection 16 simultaneously applies an asymmetrical lateral pressure on the captured structure. By the simultaneous combination of the application of an asymmetrical radial inward pressure by the resiliency of the discs on the captured structure, and the lateral pressure on the structure by the tendency of the discs to return to their rest position, the anatomical structure is ligated regardless of any small differences in the diameter of the tubular structures. Such an occluding member may be efficiently used for permanent or temporary female sterilization either by a knuckle in the Fallopian tube or by ligating the neck of the fimbria.

For such permanent female sterilization, the annular bodies may have an outer diameter of 5.5 mm and an inner diameter of 2.5 mm. The bodies may be 2 mm. thick and positioned about 0.5 mm apart. It is preferred that the elastic interconnection has a circular cross-section and be about 1 mm in diameter. The onepiece, compound elastic occluding member of the embodiment of FIGS. 1A and 1B may be used for temporary sterilization if the outer diameter of the annular disc is about 8.5 mm, the inner diameter 4.5 mm and the diameter of the elastic interconnection 1.5 mm. The other dimensions of the embodiments of the occluding member of FIGS. 1A and 1B for temporary sterilization are the same as those for permanent sterilization.

Figure 8:
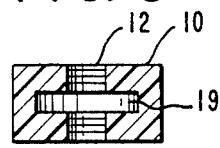
FIG. 8 is a cross-sectional view of an illustrative body of the one-piece, compound elastic occluding member of the invention showing an internal annular channel for receiving an anesthetic agent.

It is preferred that the occluding member has means for applying an anesthetic agent directly to the tubular structure captured by the occluding member. Such means may be striations 17 on the inside of the apertures in the discs 10. For example, the striations may be in the form of grooves in the inner surface of the members about 0.4 mm deep. The anesthetic agents may include Xylocaine or Marcaine and be in the form of a jelly, a powder or a solution. Alternatively, as shown in FIG. 8, the anesthetic may be included in a channel 19 formed in the inner surface of the discs.

In the embodiment of FIGS. 2A and 2B, the discs 10 are congruent both in the rest position and in the operative position. In this embodiment, the discs are rotated 360° relative to each other around the resilient interconnection 16, from the rest position to the operative position, so that increased tension is placed upon the elastic interconnection in the operative position of the discs. Aside from this distinction the dimensions and operation of the occluding member of FIGS. 2A and 2B are the same as those of the embodiments of FIGS. 1A and 1B.

Figure 3A:
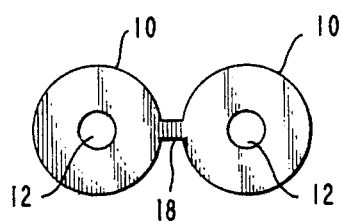
FIGS. 3A and 3B show views like FIGS. 1A and 1B of a third embodiment of the invention.
Figure 3B:
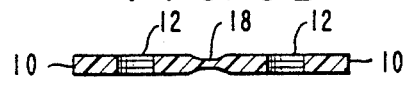

In the embodiment of FIGS. 3A and 3B, the annular bodies 10 lie in the same plane in the rest position, as shown, and are joined by an elastic interconnection 18, resulting in a dumbell-like formation. In the embodiment of FIGS. 3A and 3B, the occluding member is changed from the rest position into the operating position by pivoting the members, with respect to each other, at the edges joined by the interconnection 18. In the operative position, as shown in FIG. 4, therefore, the discs are under the tension of the interconnection 18 to return to the rest position as shown in FIGS. 3A and 3B.

Figure 4:
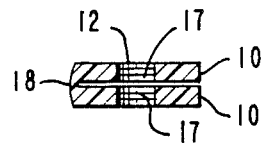
FIG. 4 is a cross-sectional, slightly enlarged, view of the embodiment of FIGS. 3A and 3B in the operative position.

It is preferred that the cross-section of the interconnection 18 be reduced toward its central portion with the result that, when the member is in the operating position, as shown in FIG. 4, the connection 18 is almost planar across the ends of the annular discs 10.

The interconnection 18 is substantially circular in cross-section and in the preferred embodiment is about 2 mm. long. The dimensions of the discs may be the same as those stated for the embodiment of FIGS. 1A and 1B and the interconnection 18 may be reduced in cross-section to a dimension of about 1 mm at the center of the interconnection.

When the occluding member of FIGS. 3A and 3B, while expanded, is forced off the barrel of the applicator, radial inward pressure is applied as in the prior embodiments, however, the asymmetrical pressure is along the length of the tubular structure.

Figure 5A:
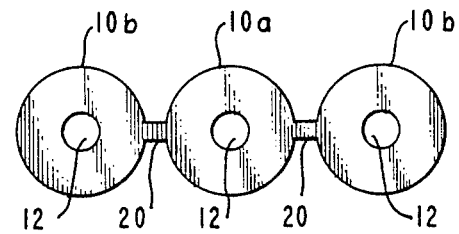
FIGS. 5A and 5B show views like FIGS. 1A and 1B of a fourth embodiment of the invention.
Figure 5B:
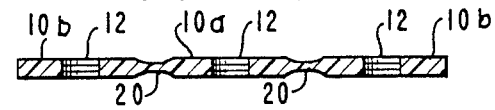

In the embodiment of FIGS. 5A and 5B, three different annular discs are interconnected and lie in the same plane in the rest position, as shown. The discs 10 are aligned and the central disc 10a is interconnected at opposing edges to the discs 10b formed as the ends of the occluding member. The discs are joined by elastic interconnections 20, each of which is similar in configuration to the elastic connection 18 of FIGS. 3A and 3B.

Figure 7:
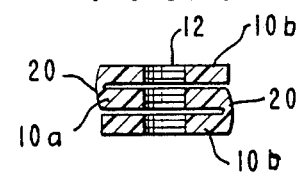
FIG. 7 is a cross-sectional view, slightly enlarged, of the embodiment of FIGS. 5A, 5B and 6, in the operative position.

In changing the embodiment of FIGS. 5A and 5B, from the rest position to the operative position, as shown in FIG. 7, the end discs 10b are pivoted about the connections 20 in opposite directions to sandwich the central disc 10a between the two end discs. The resulting configuration results in the alignment of the apertures 12 with the 3 discs being in parallel planes.

In the operation of the embodiment of FIGS. 5A and 5B, all three discs apply asymmetrical, radial, inward pressure on an anatomical structure drawn through the apertures and opposing asymmetrical lateral pressure as each of the end discs attempts to restore itself to the rest position under the tension applied to the interconnections 20. In a specific use for permanent sterilization, the annular discs may be 5.5 mm in outer diameter and 2.5 mm in inner diameter, but the discs may be thinner than in the prior embodiments resulting in a thickness of about 1.2 mm. The innerconnections 20 may be about 3 mm long and narrow to about 1 mm in the central portion. For maximum efficiency, the central portions of the connections 20 should be rounded.

It is to be understood, of course, that the stated dimensions of the annular discs of the occluding member are exemplary and other dimensions may be used. For example, in the embodiment of FIGS. 5A and 5B, the outer diameter may be 6 mm and the inner diameter, 3 mm.

Figure 6:
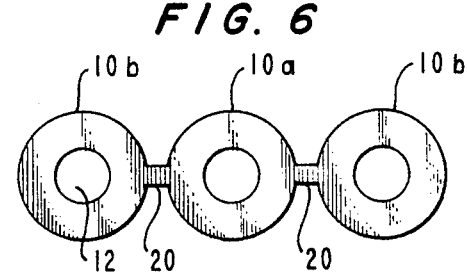
FIG. 6 shows a top view of a variation of the embodiment of FIGS. 5A and 5B.

For use of the embodiment of FIGS. 5A and 5B, for temporary sterilization, the discs are so formed as to apply less pressure on the captured anatomical structure so as to permit blood to continue to flow through the captured area. Such a variation in the embodiment of FIGS. 5A and 5B is shown in FIG. 6. In such an embodiment, for example, the outer diameter of the discs may be 8.5 mm and the inner diameter 4.5 mm. As understood by surgeons, the Fallopian tubes, for example, vary a great deal in diameter. The dimensions of the occluding member may be varied as desired to achieve permanent or temporary sterilization for various diameters of tubes.

Figure 9:
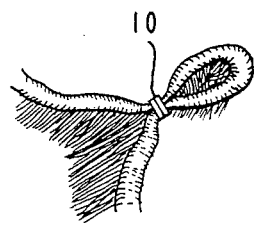
FIGS. 9 and 10 are schematic illustrations of the application of the embodiment of FIG. 1, for example, to anatomical tubular structures.
Figure 10:
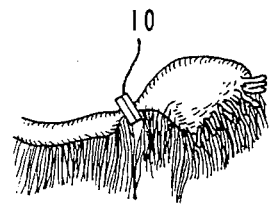

As shown in FIG. 9, a knuckle of an anatomical tubular structure has been drawn through the apertures of an embodiment of the invention such as shown in FIGS. 1A and 1B, or FIGS. 2A and 2B, and the annular discs are applying both inward radial pressure and simultaneous asymmetrical lateral pressure on the tubular structure. This is accomplished by the elasticity of the discs in returning to the unexpanded position and by the elasticity of the interconnection under which the discs attempt to return to the rest position. In the illustration of FIG. 10, the end of the Fallopian tube including the fimbria has been drawn through the apertures of the occluding member in the operative position and the ligation is applied to the neck of the fimbria. In the embodiments of FIGS. 3A and 3B, FIGS. 5A and 5B, and FIG. 6, the asymmetrical pressure will be along the length of the anatomical tubular structure rather than across the anatomical structure as shown in FIGS. 9 and 10.

It will be apparent to those skilled in the art that various modifications and variations can be made in the one-piece, compound, elastic occluding member of the present invention without departing from the scope or spirit of the invention.

What is claimed is:

1. A one-piece, compound, elastic occluding member for ligating an anatomical tubular structure comprising:
   first means for applying symmetrical, radial, inward pressure on the tubular structure; and
   second means for simultaneously applying asymmetrical, lateral pressure on the tubular structure.

2. A one-piece, compound, elastic occluding member for ligating an anatomical tubular structure comprising:
   two substantially solid, like bodies, each having a central aperture, said apertures being expandable for receiving the tubular structure drawn therethrough, each body being composed of elastic, non-tissue reactive material for applying symmetrical, radial, inward pressure on the tubular structure, the bodies having a mutually relative operative position and a rest position; said apertures being substantially axially aligned in the operating position; and
   an integral, elastic interconnection between said two bodies, the positioning of said bodies in their relative operative position placing said interconnection under stress for urging the bodies in the operative position back to the rest position and thereby for applying asymmetrical pressure on a tubular structure drawn through the aligned apertures in the operative position;
   whereby, an anatomical tubular structure drawn through said apertures while expanded and in the operative position is ligated by the release of the apertures to the elasticity of the bodies and the release of the bodies to the elasticity of the interconnection.

3. The one-piece, compound, occluding member of claim 2, wherein said bodies are annular and in parallel planes and said interconnection is an integral stud symmetrically positioned as to both bodies adjacent the outer circumferences.

4. The one-piece, compound, occluding member of claim 3, wherein said bodies overlap to include the interconnection at the rest position and are rotated relatively 180° to the operative position.

5. The one-piece, compound, occluding member of claim 3, wherein said bodies and their apertures are congruent in the rest position, and the bodies are rotated relatively 360° to the operative position.

6. The one-piece, compound, occluding member of claim 3 wherein the inner cylindrical surfaces of said annular bodies are grooved for the receipt of an anesthetic agent.

7. The one-piece, compound, occluding member of any one of claims 3, 4, 5, and 6 wherein the member may be used for permanently occluding a Fallopian tube or the neck of the fimbria and the annular bodies are 2 mm thick with inner and outer diameters of 2.5 mm and 5.5 mm, respectively, and the interconnecting stud is 0.5 mm long and 1 mm in diameter.

8. The one-piece, compound, occluding member of any one of claims 3, 4, 5 and 6 wherein the member may be used for temporarily occluding a Fallopian tube or the neck of the fimbria and the annular bodies are 2 mm thick with inner and outer diameters of 4.5 mm and 8.5 mm, respectively, and the interconnecting stud is 0.5 mm long and 1.5 mm in diameter.

9. The one-piece, compound, occluding member of claim 6 wherein said inner cylindrical surface of said annular bodies includes striations and said member includes an anesthetic agent in said striations.

10. The one-piece, compound, occluding member of claim 6 wherein said inner cylindrical surface includes an annular channel and said member includes an anesthetic agent in said channel.

11. The one-piece, compound, occluding member of either one of claims 9 and 10 wherein said anesthetic agent is selected from the group consisting of Xylocaine and Marcaine.

12. The one-piece, compound, occluding member of claim 2, wherein said bodies are substantially annular and lie in the same plane in the rest position and said interconnection is integral with the outer edges of the bodies, the bodies being substantially congruent in the operative position, the interconnection acting as a resilient hinge.

13. The one-piece, compound, occluding member of claim 12 wherein said interconnection is substantially planar in the operative position and lies in a plane substantially tangent to the edges of said bodies.

14. The one-piece, compound, occluding member of claim 12 wherein the cross section of the interconnection is reduced in the central portion.

15. The one-piece, compound, occluding member of claim 12 wherein said member includes a third like body, and a second interconnection integral with the outer edge of the third body and the outer edge of one of the two bodies, the central aperture of the third body being linearly aligned with said apertures of said two bodies, the three bodies lying in the same plane and forming two outer bodies and a central body in the rest position, and the two outer bodies being substantially congruent with the central body in the operative position, the two interconnections acting as resilient hinges.

16. The one-piece, compound, occluding member of claim 15 wherein each of said connections is substantially planar in the operative position and lie in planes substantially tangent to the edges of said bodies.

17. The one-piece, compound, occluding member of either of claims 12 and 15 wherein the inner, cylindrical surfaces of said annular bodies are grooved for the receipt of an anesthetic agent.

18. The one-piece, compound, occluding member of claim 17 wherein said inner cylindrical surface of said annular bodies includes striations and said member includes an anesthetic agent in said striations.

19. The one-piece, compound, occluding member of claim 18 wherein said anesthetic agent is selected from the group consisting of Xylocaine and Marcaine.

20. The one-piece, compound, occluding member of claim 17 wherein said inner cylindrical surface of said annular bodies includes an annular channel and said member includes an anesthetic agent in said channel.

21. The one-piece, compound, occluding member of claim 15 wherein the member may be used for permanently occluding a Fallopian tube or the neck of the fimbria and each of the annular bodies is 1.2 mm thick with inner and outer diameters of 2.5 mm and 5.5 mm, respectively, and the interconnections are 2 mm wide, 3 mm long, with their cross sections reduced to 1 mm at their central portions.

22. The one-piece, compound, occluding member of claim 12 wherein the member may be used for temporarily occluding a Fallopian tube or the neck of the fimbria and each of the annular bodies is 1.2 mm thick with inner and outer diameters of 4.5 mm and 8.5 mm, respectively, and the interconnections are 2 mm wide, 3 mm long with their cross sections reduced to 1 mm at their central portions.

23. A one-piece, compound, elastic occluding member for ligating an anatomical tubular structure comprising:

a pair of parallel, unbroken, solid, like bodies, each having a central aperture, said apertures being aligned and expandable for receiving the tubular structure drawn therethrough, each body being composed of elastic, non-tissue reactive material for applying symmetrical, radial, inward pressure on the tubular structure drawn through the apertures, and at least one short elastic integral interconnection between said bodies simultaneously applying asymmetrical lateral pressure on the tubular structure.

24. The occluding member of claim 23 wherein said pair of like parallel bodies are spaced apart by about 0.5 mm.

* * * * *